United States Patent
Kawasaki et al.

(10) Patent No.: US 6,855,774 B2
(45) Date of Patent: Feb. 15, 2005

(54) CROSSLINKABLE ELASTOMER COMPOSITION

(75) Inventors: Kazuyoshi Kawasaki, Settsu (JP); Tsuyoshi Itagaki, Tsukuba (JP); Katsuhiko Iseki, Tsuchiura (JP); Takafumi Yamato, Settsu (JP); Tsuyoshi Noguchi, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 78 days.

(21) Appl. No.: 10/311,803

(22) PCT Filed: May 22, 2001

(86) PCT No.: PCT/JP01/04262

§ 371 (c)(1),
(2), (4) Date: Feb. 11, 2003

(87) PCT Pub. No.: WO02/00781

PCT Pub. Date: Jan. 3, 2002

(65) Prior Publication Data

US 2003/0191247 A1 Oct. 9, 2003

(30) Foreign Application Priority Data

Feb. 11, 2003 (JP) ........................................ 2000-193480

(51) Int. Cl.[7] .............................................. C08F 114/18
(52) U.S. Cl. .................. 525/326.2; 524/279; 525/242; 525/374
(58) Field of Search .............................. 525/326.2, 374, 525/242; 524/279

(56) References Cited

U.S. PATENT DOCUMENTS

| | | | | |
|---|---|---|---|---|
| 5,767,204 A | * | 6/1998 | Iwa et al. | ................ 525/359.3 |
| 6,500,545 B1 | * | 12/2002 | Ambrose et al. | ........... 428/413 |

FOREIGN PATENT DOCUMENTS

| EP | 0110420 | * | 6/1984 |
| EP | 0705873 A1 | * | 4/1996 |
| JP | 59-109546 | * | 6/1984 |
| JP | 5-112509 | | 5/1993 |
| JP | 8-120146 | | 5/1996 |
| JP | 08-120146 | * | 5/1996 |

* cited by examiner

Primary Examiner—David W. Wu
Assistant Examiner—Henry S. Hu
(74) Attorney, Agent, or Firm—Sughrue Mion, PLLC (57) ABSTRACT

A crosslinkable elastomer composition which provides a crosslinked product with improved mechanical strength and heat resistance, comprising, (A) a compound having at least two crosslinkable groups represented by the formula (I):

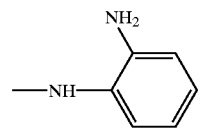

and (B) an elastomer which contains a crosslinking site capable of reacting with the crosslinkable group (I) is prepared.

16 Claims, 1 Drawing Sheet

FIG. 1

CROSSLINKABLE ELASTOMER COMPOSITION

TECHNICAL FIELD

The present invention relates to a crosslinkable elastomer composition, particularly a flourine-containing crosslinkable elastomer composition which can provide a molded article of a crosslinked rubber with superior sealing property, mechanical strength and heat resistance at a high temperature.

BACKGROUND ART

Because flourine-containing elastomer, especially perfluoro elasotmer which is composed mainly of tetrafluoroethylene (TFE) units, demonstrates excellent chemical resistance, solvent resistance and heat resistance, it is widely used as a sealing material and the like under harsh circumstances.

However, the characteristics in demand have become more severe as technology advances, and in the fields of aerospace, semiconductor manufacturing devices and chemical plant, sealing property under high temperature circumstances of at least 300° C. is desired.

In response to such demands, an approach to improve heat resistance by exercising ingenuity to the crosslinking system has been suggested. As methods of these, a toriazine crosslinking system, using a flourine-containing elastomer with a nitrile group introduced as the crosslinking point, to form a triazine ring in the presence of an organic tin compound (for example JP-A-58-152041) is known. Other known crosslinking systems are, for example, an oxazole crosslinking system in which an oxazole ring is formed in the presence of bisaminophenol, (for example JP-A-59-109546), an imidazole crosslinking system in which a imidazole ring is formed in the presence of a tetramin compound, (for example JP-A-59-109546), and an thiazole crosslinking system in which an thiazole ring is formed in the presence of bisaminothiophenol, (for example JP-A-8-104789). In these latter systems flourine-containing elastomer with a nitrile group is also introduced as the crosslinking point.

Of these crosslinking systems, when crosslinking a nitrile group containing perfluoro elasotmer with a tetramin compound, the heat resistance of the obtained molded article of the crosslinked rubber will improve in comparison to the conventional. However, in high temperatures exceeding 300° C., deterioration is intense in contrast to a toriazine crosslinking system or an oxazole crosslinking system.

An object of the present invention is to provide a crosslinkable elastomer composition to produce a molded article of the crosslinkable rubber, improved especially in mechanical strength and heat resistance at a high temperature.

Another object of the present invention is to provide a new crosslinking agent.

DISCLOSURE OF INVENTION

The present invention relates to a crosslinkable elastomer composition comprising (A) a compound having at least two crosslinkable groups represented by the formula (I):

and (B) an elastomer which contains a crosslinking site capable of reacting with the crosslinkable group (I).

It has not been found that this compound (A) works as a crosslinking agent, and the compound (A) is thus a new crosslinking agent.

As for the compound (A), a compound represented by the formula (II):

in which $R^1$ represents a substituted or non-substituted alkylene group, a substituted or non-substituted arylene group, or a group represented by the formula (III):

in which $R^2$ represents —$SO_2$—, —O—, —CO—, a substituted or non-substituted alkylene group, or a single bonding, are preferably exemplified.

As for the elastomer (B), a fluorine-containing elastomer, a perfluoro elastomer in particular, which contains at least a functional group selected from the group consisting of a nitrile group, a carboxyl group and an alkoxycarbonyl group is preferably used.

Among the compounds (A), a compound represented by the formula (IV):

in which $R^3$ is is a new compound which is to be included in the scope of the present invention.

The present invention also relates to a molded article of a crosslinked rubber, obtained by crosslinking the crosslinkable elastomer composition.

BEST MODE FOR CARRYING OUT THE INVENTION

The crosslinking system made when the crosslinkable elastomer composition of the present invention is crosslinked is similar to an imidazole crosslinking system. A conventional imidazole crosslinking forms a crosslinking structure, for example, such as

On the other hand, in the present invention, as shown in it is presumed that the benzimidazole ring formation without a H—N bond contributes greatly to the improvement of heat resistance. Consequently, compound (A), which functions as a crosslinking agent, is an important factor of the present invention. The following is a description of compound (A).

In order to form the crosslinking structure, compound (A) contains at least two, preferably two to three, most preferably two crosslinkable groups (I) represented by the formula (I).

As compound (A), a compound represented by the formula (II):

which contains two crosslinkable groups (I) is preferred from the viewpoint that synthesis is conducted with ease. $R^1$ and $R^2$ in the formula are as indicated above.

In the formula (III), $R^2$ is —$SO_2$—, —O—, —CO—, substituted or non-substituted alkylene group, or a single bonding.

Substituted or non-substituted alkylene group of $R^1$ is for example, methylene, ethylene, butylene, and the like.

Substituted or non-substituted arylene group of $R^1$ is for example, phenylene, and the like.

Preferred examples of the substituted or non-substituted alkylene group of $R^2$ in the formula (III), though not limited to these, are non-substituted alkylene groups having 1 to 6 carbon atoms and fluoroalkylene groups having 1 to 10 carbon atoms. As the fluoroalkylene group, and the like can be given. These $R^2$ are also known as examples of bisdiaminophenyl compounds in JP-B-2-59177 and JP-A-8-120146.

$R^2$ may be bonded to any positions of the both right and left benzene rings, but from the viewpoint that synthesis is conducted with ease and the crosslinking reaction is easily advanced, it is preferred that $R^2$ is so bonded as to be at a para position or meta position with —NH— group.

Preferable examples of the compound (A) are a compound represented by the formula (IV):

in which R represents —$SO_2$—, —O—, —CO—, a substituted or non-substituted alkylene group, or

Examples thereof, though not limited to these, are 2,2-bis-[N-(2-aminophenyl)-(4-aminophenyl)]hexafluoropropane, 2,2-bis-[N-(2-aminophenyl)-3-(3-aminophenyl)]hexafluoropropane, 2,2-bis-[N-(2-aminophenyl)-{4-(4-aminophenoxy)phenyl}]hexafluoropropane, N,N'-di(2-aminophenyl)-4,4'-diaminodiphenyl, N,N'-di(2-aminophenyl)-4,4'-diaminophenylether, N,N'-di(2-aminophenyl)-p-phenylenediamine and the like.

The compounds (A) explained above are a new crosslinking agent which can provide a crosslinked product with excellent mechanical strength, heat resistance and chemical resistance, and in particular, well-balanced heat resistance and chemical resistance.

Furthermore, among the compounds (A), a compound represented by the formula (IV):

in which $R^3$ is is a new compound.

These new compounds can be prepared by introducing nitro groups to each corresponding 2,2-bis-(4-aminophenyl)hexafluoropropane (or 2,2-bis-(3-aminophenyl)hexafluoropropane) or 2,2-bis-[4-(4-aminophenoxy)phenyl]hexafluoropropane with o-fluoronitrobenzene, reducing the system in the presence of palladium carbon and the like.

Other compounds included in the category of the compound represented by the formula (II) are described in U.S. Pat. No. 3,708,439. Though purifying methods are slightly different, the process of synthesizing the compound represented by (IV) can be basically applied as it is.

The following is a description of the crosslinkable elastomer which is the component (B).

As the crosslinkable elastomer (B), one having a crosslinking site capable of reacting with the crosslinkable group (I) with excellent heat resistance may be preferable, and fluorine-containing elastomers can be given.

As the crosslinking site capable of reacting with the crosslinkable group (I), a nitrile group (—CN), carboxyl group (—COOH), alkoxycarbonyl group (—COOR in which R is an alkyl group having 1 to 3 carbon atoms) and the like can be given.

The fluorine-containing elastomer is preferably one represented by the formula (V):

$$X^1\text{-}[A\text{-}(Y)_p]_q\text{—}X^2 \qquad (V)$$

or the formula (VI):

$$X^1\text{-}[A\text{-}(Y^1)_p]_q\text{—}[B\text{—}(Y^2)_r]_s\text{—}X^2 \qquad (VI)$$

in which $X^1$ and $X^2$ can be varied without any restriction by changing the initiator or chain transfer agent for the polymerization or by modifying the terminal group, $X^1$ and $X^2$ may be the same or different, and each of $X^1$ and $X^2$ being a carboxyl group, alkoxycarbonyl group, nitrile group, iodine atom, bromine atom or sulfonate group; Y, $Y^1$ and $Y^2$ are the same or different, and each of Y, $Y^1$ and $Y^2$ is a divalent organic group containing a carboxyl group, alkoxycarbonyl group or nitrile group in the side chain; A is a fluorine-containing elastomeric polymer chain segment (hereinafter elastomeric segment A); B is a fluorine-containing non-elastomeric polymer chain segment (hereinafter non-elastomeric segment B); p is an integer of 0 to 50, q is an integer of 1 to 5, r is an integer of 0 to 10, s is an integer of 1 to 3; and any one of $X^1$, $X^2$, Y, $Y^1$ and $Y^2$ is a nitrile group, carboxyl group or alkoxycarbonyl group, while Y, $Y^1$ or $Y^2$ may be randomly included in the segment A or B. In addition, a fluorine-containing elastomer which has, as the crosslinking site, a carboxyl group, nitrile group, and/or alkoxy carbonyl group at the terminal of the main chain or in the branched chain is preferable.

Examples of the elastomeric segment A are a perfluoro elastomeric segment such as a two-segment copolymer rubber represented by the formula (1):

in which m/n=95 to 50/5 to 50 (% by mole) and $R_f$ is a fluoropolyoxyalkyl group having 1 to 20 carbon atoms or perfluoroalkyl group having 1 to 8 carbon atoms or a three-segment copolymer rubber represented by the formula (2):

in which l/m/n=95 to 35/0 to 30/5 to 35 (% by mole) and $R_f$ is a fluoropolyoxyalkyl group having 1 to 20 carbon atoms or perfluoroalkyl group having 1 to 8 carbon atoms; or a non-perfluoro elastomeric segment such as a two-segment copolymer rubber represented by the formula (3):

in which m/n=85 to 60/15 to 40 (% by mole), a three-segment copolymer rubber represented by the formula (4):

in which l/m/n=85 to 20/0 to 40/15 to 40 (% by mole), a three-segment copolymer rubber represented by the formula (5):

in which l/m/n=95 to 45/0 to 10/5 to 45 (% by mole), each of $Z^1$, $Z^2$ and $Z^3$ is individually a fluorine atom or hydrogen atom, $R_f$ is a fluoropolyoxyalkyl group having 1 to 20 carbon atoms or perfluoroalkyl group having 1 to 8 carbon atoms, in which l/m=20/80 to 80/20% by mole, in which l/m=80/20 to 50/50% by mole, in which l/m/n=1 to 80/0 to 80/10 to 50% by mole, and $R_f$ is as defined above.

Examples of Y, $Y^1$ and $Y^2$ which introduces the crosslinking point to the branched chain are a nitrile group-containing monomer, carboxyl group-containing monomer and alkoxycarbonyl group-containing monomer, represented by the following formulas:

in which m is 0 to 5 and n is 1 to 8, in which n is 1 to 4, in which n is 2 to 5, in which n is 1 to 6, in which n is 1 to 5, or in which n is of 0 to 5,

[$X^3$ being CN, COOH or COOR$^5$ (in which $R^5$ is an alkyl group which has 1 to 10 carbon atoms and may contain a fluorine atom)].

Among them, the nitrile group-containing monomer and carboxyl group-containing monomer are usually preferred.

As for the kind of the non-elastomeric segment B, there is no particular limitation, as long as it contains a fluorine atom and does not have the above elastomeric property. A suitable non-elastometric segment may be selected depending on the desired properties or functions of the polymer to be obtained by block copolymerization. Among these segments, when mechanical properties are requested, a crystalline polymer chain segment, of which the melting point of the crystal is at least 150° C., is preferable.

Examples of monomers constituting the non-elastomeric segment B, fluorine-containing monomers in particular, are one or at least two of perhalo olefins such as TFE, chlorotrifluoroethylene (CTFE), perfluoro(alkyl vinyl ether) (PAVE), hexafluoropropylene (HFP), $CF_2=CF(CF_2)_pX$, (p is an integer of 1 to 10, X is F or Cl) and perfluoro-2-butene; and partially fluorinated olefins such as vinylidene fluoride, vinyl fluoride, trifluoroethylene, (each of $X^4$ and $X^5$ is H or F and q is an integer of 1 to 10), and $CH_2=C(CF_3)_2$. Furthermore, one or at least two of monomers copolymerizable therewith, such as ethylene, propylene, vinyl chloride, vinyl ethers, carboxylate vinyl esters, and acrylic acids and acrylates may also be used as a component of copolymerization.

Among these, as the main component monomer, a fluorine-containing olefin alone, combination of fluorine-containing olefins, combination of ethylene and TFE, and combination of ethylene and CTFE are preferable from the viewpoint of chemical resistance and heat resistance. In particular, a perhalo olefin alone and combination of perhalo olefins are preferable.

Specifically,
(1) VdF/TFE (0 to 100/100 to 0), particularly VdF/TFE (70 to 99/30 to 1), PTFE or PVdF;
(2) ethylene/TFE/HFP (6 to 60/40 to 81/1 to 30), 3,3,3-trifluoropropylene-1,2-trifluoromethyl-3,3,3-trifluoropropyl-1-ene/PAVE (40 to 60/60 to 40);
(3) TFE/$CF_2=CF—R_f^3$ (in such an amount that the non-elastomeric property is exhibited, i.e., the amount of $CF_2=CF—R_f^3$ is not more than 15% by mole; $R_f^3$ is a linear or branched fluoro or perfluoro alkyl group or a fluoro or perfluoro oxyalkyl group, which may contain at least one ether type oxygen atom);
(4) VdF/TFE/CTFE (50 to 99/30 to 0/20 to 1);
(5) VdF/TFE/HFP (60 to 99/30 to 0/10 to 1);
(6) ethylene/TFE (30 to 60/70 to 40);
(7) polychlorotrifluoroethylene (PCTFE);
(8) ethylene/CTFE (30 to 60/70 to 40);
and the like can be given. The unit of values in the parentheses is % by mole. Of these, PTFE and non-elastomeric copolymer of TFE/$CF_2=CF—R_f^3$ ($Rf^3$ is as defined above) are particularly preferable from the viewpoint of chemical resistance and heat resistance.

In addition, as a monomer which may constitute the non-elastomeric segment B, the above-mentioned unit $Y^2$ which creates curing site may be introduced in an amount of at most 5% by mole, preferably at most 2% by mole.

The block copolymerization of the non-elastomeric segment B can be carried out, for example, after the emulsion polymerization of the elastomeric segment A, by exchanging the monomers to those for the non-elastomeric segment B.

The number average molecular weight of the non-elastomeric segment B can be adjusted extensively, from 1,000 to 1,200,000, preferably from 3,000 to 400,000.

Also, by making the proportion of perhalo olefin at least 90% by mole, in particular at least 95% by mole in the units constituting the elastomeric segment A, the block copolymerization of the non-elastomeric segment B to the elastomeric segment A is assured, and in addition, the molecular weight of the non-elastomeric segment B (polymerization degree) can be increased.

The terminal groups of the elastomers, i.e., $X^1$ and $X^2$, are not particularly limited as mentioned above, but preferably a carboxyl group, alkoxycarbonyl group or nitrile group. As the method of introducing these functional groups to the terminal group, acid treatment mentioned later can be given.

The above fluorine-containing elastomer can be produced by polymerization methods such as emulsion polymerization, suspension polymerization, and solution polymerization.

As a polymerization initiator, one which is capable of making a carboxyl group or a group capable of generating a carboxyl group (for example, carboxyl fluoride, carboxyl chloride, $CF_2OH$, all of which generate a carboxyl group in the presence of water) present in the elastomer terminal is preferably used. Examples are ammonium persulfate (APS), potassium persulfate (KPS) and the like.

Furthermore, a chain transfer agent which is generally used to adjust molecular weight can be used, but it is preferable that it is used as little as possible, as it decreases the ratio of groups capable of generating carboxyl groups, which are to be introduced into the terminal. However, this does not apply when the chain transfer agent is capable of making the above group present in the elastomer terminal. When a chain transfer agent is not used, the molecular weight can be adjusted by conducting polymerization under low pressure, for example less than 2 MPa·G, more preferably at most 1 MPa·G. Other polymerization conditions are not particularly limited. However, in order to obtain polymerization products which have a carboxyl group in the terminal and/or the branched chain, without acid treatment, it is preferable that the pH of the polymerization system is set to a strongly acidic value of at most pH 3.

Some of the polymerization products obtained in this way do not include free carboxyl groups depending on the polymerization conditions, but by subjecting to the following acid treatment, those groups can be converted into free carboxyl groups.

As for the fluorine-containing elastomer used in the present invention, it is preferable to convert groups such as a metallic salt and an ammonium salt of carboxylic acid present in the polymerization products into a carboxyl group by subjecting the polymerization products to acid treatment. As methods of acid treatment, the methods of washing with hydrochloric acid, sulfuric acid or nitric acid or setting the pH of the system after the polymerization reaction to at most pH 3 with these acids are appropriate.

From the viewpoint of simplifying the process, it is preferable that this acid treatment is applied as an agglomeration measure when isolating the polymerization products from the polymerization reaction mixture by agglomeration. It is also possible to subject the polymerization mixture to acid treatment and then isolate the polymer products by means of lyophilization. Furthermore, methods such as agglomeration by ultrasonic waves and the like or agglomeration by mechanical power can be adopted.

Also, it is possible to oxidize fluorine-containing elastomers having iodine and bromine by fuming sulfic acid and then introduce a carboxyl group.

The amount of compound (A) which is a crosslinking agent is preferable 0.1 to 10 parts by weight based on 100 parts by weight of the elastomer.

In the composition of the present invention, the usual additives to be compounded into the crosslinkable elastomer composition such as a filler, processing aid, plasticizer and colorant may be compounded according to need. One type or more than one type of commonly used crosslinking agents and crosslinking accelerators that differ from those listed above may also be compounded. Furthermore, more than two types of elastomers may be compounded, within the range of the effects of the present invention not being spoiled.

The composition of the present invention can be prepared by mixing the above components by using a typical rubber-processing machine such as an open roll, Banbury mixer or kneader. It can also be prepared by the methods of using an internal mixer or co-coagulating from mixed emulsion.

For producing a pre-molded article from the above-mentioned composition, usual known methods may be employed, such as the method of heating and compressing in a metal mold, the method of putting in a heated metal mold under pressure and the method of extruding with an extruder can be conducted. Extruded products such as a hose and electric wire are capable of maintaining its form after extrusion and therefore, the pre-molded article which is extruded without using a crosslinking agent can be utilized as it is. It is also possible to use a pre-molded article made by subjecting to crosslinking by heating with steam using a crosslinking agent. Also, when it is difficult to maintain the form of shaped product such as an O-ring in an uncrosslinked state after mold-releasing, it becomes possible to hold the shape by using a pre-molded article which is crosslinked in advance using a crosslinking agent.

As the crosslinking temperature, a relatively low crosslinking temperature (for example 150 to 230° C., preferably 170 to 200° C.) provides a crosslinked product with good properties.

The obtained crosslinked product is new also as a compound and provides high heat resistance which could not be obtained by prior imizadole crosslinking, and in addition, superior mechanical strength and chemical resistance.

The new crosslinked product, represented by the formula (VII):

($R^1$ in the formula is as stated before) is an ultra high molecular weight polymer which has an imizadole ring in the crosslinking site.

This crosslinked product has high heat resistance, superior mechanical strength and chemical resistance, and the variation over time of the permanent compression strain at a high temperature, a standard for evaluating sealing property, has become particularly small, and this characteristic is essential to sealing materials.

The crosslinked product of the present invention is effective as various molded articles in the fields indicated in the following Tables 1, 2 and 3.

TABLE 1

| Field of industry | Sub-field of industry | Final product | Equipment |
|---|---|---|---|
| Electrical | Semi-conductor | Semi-conductor production apparatus | CVD equipment |
| | | Liquid crystal panel production apparatus | Dry etching equipment |
| | | Plasma panel production apparatus | Wet etching equipment |
| | | | Oxidation and diffusion equipment |
| | | | Sputtering equipment |
| | | | Ashing equipment |
| | | | Cleaning equipment |
| | | | Ion implantation equipment |
| Transportation | Vehicle | Car | Engine and auxiliary equipment |
| | | | Automatic transmission |
| | | | Fuel line and auxiliary equipment |
| | Aircraft | Aircraft | Fuel line |
| | Rocket | Rocket | Fuel line |
| | Ship | Ship | Fuel line |
| Parts | | | |
| O (square) ring, packing, sealing material, tube, roll | | | |
| Coating, lining, gasket, diaphragm, hose | | | |
| Gasket, shaft seal, valve stem seal, sealing material, hose | | | |
| Hose, sealing material | | | |
| O (square) ring, tube, packing, core material of valve, hose, sealing material, diaphragm | | | |
| Diaphragm, O (square) ring, valve, tube, packing, hose, sealing material | | | |
| " | | | |
| " | | | |
| Chemical | Chemical products | Plant | Production line of chemicals such as pharmaceutical, agricultural chemical, coating and resin (Petroleum) |
| | Chemicals | Pharmaceuticals | Plug for chemicals |
| Mechanical | Photograph | Developing machine | Film developing machine |
| | | | X-ray film developing machine |
| | Printing | Printing machine | Printing roll |
| | Coating | Coating facilities | Coating roll |
| | Analyzer and physical and chemical appliances | | |
| Food | Plant | | Food processing line |
| Metal | Steel making | Steel sheet processing facilities | Steel sheet processing roll |
| Lining, valve, packing, roll, hose, diaphragm, O (square) ring, tube, sealing material | | | |
| Plug for chemicals | | | |
| Roll | | | |
| Roll | | | |
| Roll | | | |
| Roll | | | |
| Tube | | | |
| Lining, valve, packing, roll, hose, diaphragm, 0 (square) ring, tube, sealing material | | | |
| Roll | | | |

TABLE 2

| Field of Industry | Characteristics Required |
|---|---|
| Electrical | Plasma resistance, acid resistance, alkali resistance, amine resistance, ozone resistance, gas resistance, chemical resistance, cleanliness, heat resistance |
| Transportation | Heat resistance, amine resistance |
| | Heat resistance, amine resistance |
| | Fuel resistance, fuel permeability, heat resistance |
| | Fuel resistance, fuel permeability, heat resistance |
| | Fuel resistance, fuel permeability, heat resistance |
| | Fuel resistance, fuel permeability, heat resistance |
| Chemical | Chemical resistance, solvent resistance, heat resistance |
| | Chemical resistance, solvent resistance, heat resistance |
| | Cleanliness |
| Mechanical | Chemical resistance |
| | Chemical resistance |
| | Solvent resistance |
| | Solvent resistance |
| Food | Chemical resistance, solvent resistance, heat resistance |
| Metal | Heat resistance, acid resistance |

TABLE 3

| Field of industry | Parts |
|---|---|
| Electrical | O ring and sealing material for gate valve of corresponding product or equipment |
| | O ring and sealing material for quartz window of corresponding product or equipment |
| | O ring and sealing material for chamber of corresponding product or equipment |
| | O ring and sealing material for gate of corresponding product or equipment |
| | O ring and sealing material for bell jar of corresponding product or equipment |
| | O ring and sealing material for coupling of corresponding product or equipment |
| | O ring and sealing material for pump of corresponding product or equipment |
| | O ring and sealing material for gas controller for semiconductor of corresponding product or equipment |
| | O ring and sealing material for resist developing and releasing solutions |
| | O ring and sealing material for wafer cleaning solution |
| | Diaphragm of pump for corresponding production equipment |
| | Hose for resist developing and releasing solutions |
| | Hose and tube for wafer cleaning solution |
| | Roll for transferring wafer |
| | Lining and coating of tanks for resist developing and releasing solutions |
| | Lining and coating of tanks for wafer cleaning solution |
| | Lining and coating of tanks for wet etching |
| Transportation | Engine head gasket |
| | Metal gasket |
| | Crank shaft seal |
| | Cam shaft seal |
| | Valve stem seal |
| | Manifold packing |
| | Oil hose |
| | ATF hose |
| | Injector O ring |
| | Injector packing |
| | O ring and diaphragm for fuel pump |
| | Fuel hose |
| Chemical | |
| Mechanical | Developing roll |
| | Developing roll |
| | Gravure roll |
| | Guide roll |
| | Gravure roll for magnetic tape production and coating line |
| | Guide roll for magnetic tape production and coating line |
| | Various coating rolls |
| Food | |
| Metal | |

More specifically, the crosslinked product of the present invention can be used for the following semiconductor manufacturing equipment.

(1) Etching system
  Dry etching equipment
    Plasma etching machine
    Reactive ion etching machine
    Reactive ion beam etching machine
    Sputter etching machine
    Ion beam etching machine
  Wet etching equipment
  Ashing equipment (2) Cleaning system
  Dry etching cleaning equipment
    UV/$O_3$ cleaning machine
    Ion beam cleaning machine
    Laser beam cleaning machine
    Plasma cleaning machine
    Gas etching cleaning machine
  Extractive cleaning equipment
    Soxhlet extractive cleaning machine
    High temperature high pressure extractive cleaning machine
    Microwave extractive cleaning machine
    Supercritical extractive cleaning machine (3) Exposing system
  Stepper
  Coater and developer (4) Polishing system
  CMP equipment (5) Film forming system
  CVD equipment
  Sputtering equipment (6) Diffusion and ion implantation system
  Oxidation and diffusion equipment
  Ion implantation equipment

The crosslinked product of the present invention is suitable for sealing materials used under a high temperature condition of at least 300° C., such as sealing material for $O_2$ sensor in automobile engines, aerospace equipment engines, and oil rigs.

The present invention is then explained by means of examples, but is not limited to them.

PREPARATION EXAMPLE 1

(Synthesis of CN Group-containing Elastomer)

A 3-liter stainless steel autoclave without ignition source was charged with 1 liter of pure water, 10 g of as an emulsifying agent and 0.09 g of disodium hydrogen phosphate·12 $H_2O$ as a pH regulator. After the atmosphere in the system was replaced with nitrogen gas sufficiently to deaerate the system, the autoclave was heated to 53° C. while stirring at 600 rpm, and a mixed gas of tetrafluoroethylene (TFE) and perfluoro(methyl vinyl ether) (PMVE) (TFE/PMVE=25/75 in mole ratio) was fed so that the inside pressure became 0.78 MPa·G. Then 20 ml of an aqueous solution containing ammonium persulfate (APS) in a concentration of 264 mg/ml was fed with pressurized nitrogen to initiate the reaction.

When the inside pressure lowered to 0.69 MPa·G with the advance of the polymerization, 1.8 g of $CF_2=CFOCF_2CF(CF_3)OCF_2CF_2CN$ (CNVE) was fed with pressurized nitrogen. Then 4.7 g of TFE and 5.3 g of PMVE were fed with their self-pressure so that the inside pressure became 0.78 MPa·G. After that, as the reaction proceeds, TFE and PMVE were fed under pressure in the same manner, and pressure increase and pressure decrease were repeated between 0.78 MPa·G and 0.69 MPa·G. At the moment when the total amount of TFE and PMVE reached 70 g, 1.8 g of CNVE was fed with pressurized nitrogen.

Six hours after the initiation of the polymerization reaction, when the total amount of TFE and PMVE reached 130 g, the autoclave was cooled and an un-reacted monomer was released to prepare 1,150 g of an aqueous dispersion having a solid content of 11.3% by weight.

Then 1,000 g of the aqueous dispersion was diluted with 3,000 g of water and slowly added to 2,800 g of aqueous solution of 3.5% by weight of hydrochloric acid with stirring. After the addition, the solution was stirred for 5 minutes and the precipitated product was filtrated. Further, the obtained polymer was added to 2 kg of HCFC-141b, stirred for 5 minutes and then filtrated again. After that, the steps of washing with HCFC-141b and filtrating were repeated four times, followed by vacuum-drying at 60° C. for 72 hours to obtain 110 g of a copolymer (nitrile group-containing elastomer).

As a result of $^{19}$F-NMR analysis, the monomer units of the copolymer were TFE/PMVE/CNVE=59.8/39.6/0.6 in % by mole. Measurement was carried out according to the infrared spectroscopic analysis, and the chart shown in FIG. 1 was obtained.

Figure 1:
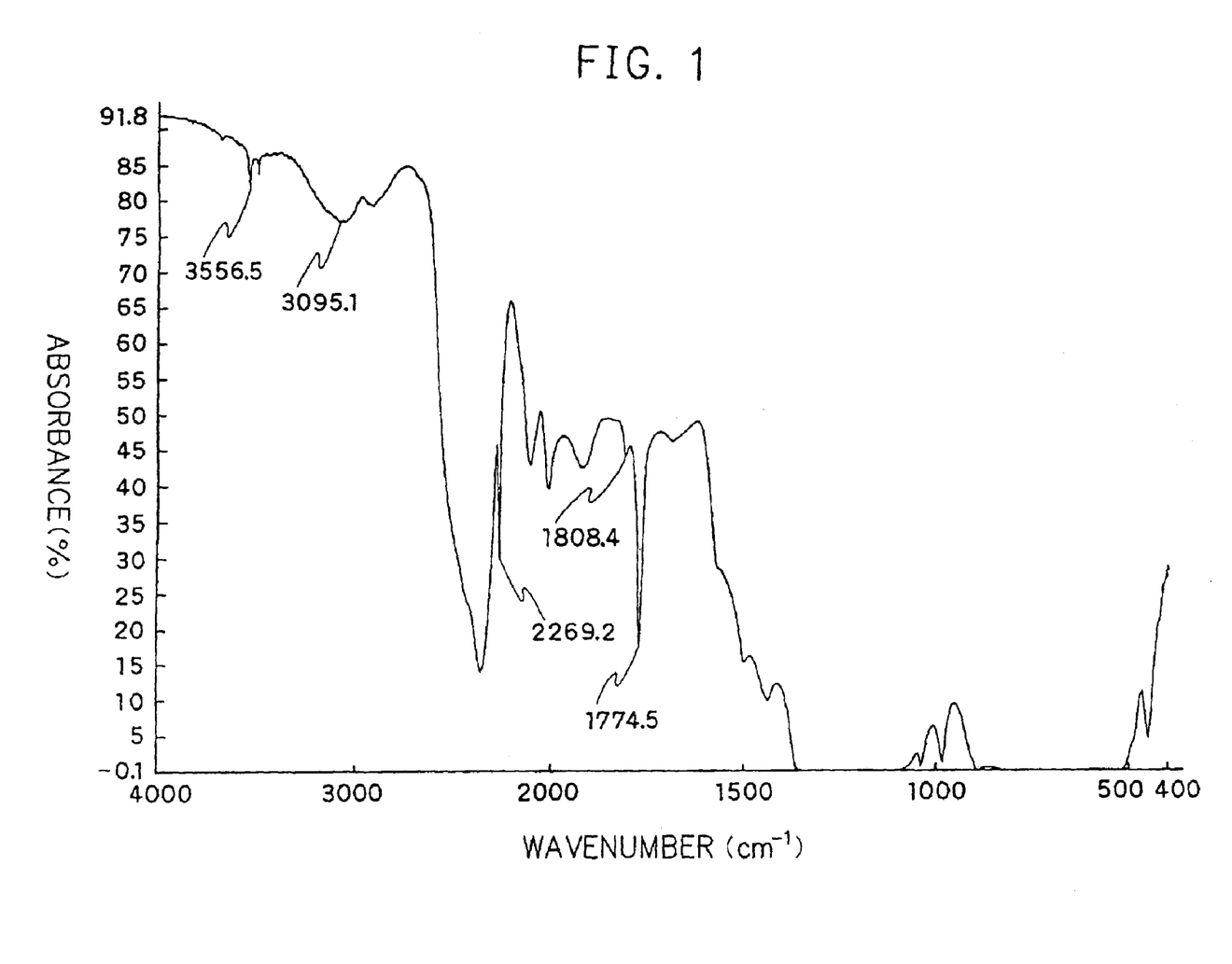
FIG. 1 is a chart of the infrared spectroscopic analysis of the fluorine-containing elastomer having a CN group, obtained in Preparation Example 1.

In the chart shown in FIG. 1, characteristic absorption of the nitrile group is found in the area of 269.2 cm$^{-1}$, characteristic absorption of the carboxyl group in the area of 1774.5 cm$^{-1}$, and 1808.4 cm$^{-1}$, and characteristic absorption of the OH group in the area of 3556.5 cm$^{-1}$ and 3095.1 cm$^{-1}$.

SYNTHESIS EXAMPLE 1

Synthesis of (2,2-bis[N-(2-nitrophenyl)-(4-aminophenyl)]hexafluoropropane

In the followings, all the reactions were conducted under a nitrogen atmosphere, and the reagents and solvents used had been dehydrated.

An autoclave was charged with 20 g (59.8 mmol) of 2,2-bis(4-aminophenyl)hexafluoropropane, 15.8 ml (150.2 mmol) of o-fluoronitrobenzene, 13.5 g (335 mmol) of magnesium oxide and 100 ml of water, and the temperature of the autoclave was elevated to 250° C. with stirring. The reaction was continued for 12 hours at the same temperature. After the completion of the reaction, the system was cooled to the room temperature, and 800 ml of ethyl acetate and 300 ml of water were added thereto. Stirring was continued until the generated substance was dissolved in ethyl acetate. The obtained solution was filtered with cerite, and extraction with ethyl acetate was conducted twice. Washing was carried out with 1N-hydrochloric acid, saturated aqueous solution of sodium hydrogen carbonate and then with saturated saline, followed by drying with absolute magnesium persulfate, and the solvent was removed under reduced pressure. The resulting crude product was re-crystallized by using ethanol and 22.4 g of a red crystal of 2,2-bis [N-(2-nitrophenyl)-(4-aminophenyl)]hexafluoropropane was prepared (yeild: 65%).

The obtained product is a new compound which has the following properties:

Melting point: 178.3 to 179.4° C.
$^1$H-NMR (in CDCl$_3$): δ (ppm)=6.80 to 8.25 (m, 16H), 9.42 to 9.55 (broad, 2H).
$^{19}$F-NMR (in CDCl$_3$): δ (ppm)=−64.3 (s, CF$_3$).
IR(KBr): cm$^{-1}$=3350, 1606, 1578, 1510, 1348, 1258.
MS m/z=576(M+).
HRMS: C$_{27}$H$_{18}$F$_6$N$_4$O$_4$(M+).
Calculated value=576.123.
Measured value=576.122.

Synthesis of 2,2-bis[N-(2-aminophenyl)-(4-aminophenyl)]hexafluoropropane 20 g (34.7 mmol) of 2,2-bis[N-(2-nitrophenyl)-(4-aminophenyl)]hexafluoropropane synthesized above were dissolved in 200 ml of ethyl acetate. Thereto was added 1 g of 10% palladium carbon as a catalyst, and replacement with hydrogen was then carried out. After that, reaction was conducted at room temperature under a hydrogen pressure of 1.01 MPa (10 atm) for 18 hours with stirring vigorously. The obtained reaction solution was filtered with cerite to remove the catalyst, and ethyl acetate was removed under reduced pressure. The residue was re-crystallized by using a chloroform-hexane mixed solution, and ethanol-water mixed solution to obtain 17 g of 2,2-bis[N-(2-aminophenyl)-(4-aminophenyl)]hexafluoropropane (hereinafter pNPN-AF) in white solid (yeild: 95%).

The synthesized product is a new compound which has the following properties:

Melting point: 150.5 to 151.6° C.
Purity: (LC area %: silica gel column, developing solvent: acetonitrile:
0.05% aqueous solution of phosphoric acid=80:20): 98%.
$^1$H-NMR(in CDCl$_3$): δ (ppm)=6.64 to 7.26 (m, 16H), 3.00 to 3.80 (broad, 4H), 5.24 to 5.35 ppm (broad, 2H).
$^{19}$F-NMR(in CDCl$_3$): δ (ppm)=−64.7(s, CF$_3$).
IR(KBr):cm$^{-1}$=3050, 2942, 1510, 1392, 1235.
MS m/z=516(M+).
HRMS: C$_{27}$H$_{22}$F$_6$N$_4$(M+).
Calculate value=516.174.
Measured value=516.175.

SYNTHESIS EXAMPLE 2

Synthesis of 2,2-bis[N-(2-nitrophenyl)-{4-(4-aminophenoxy)phenyl}]hexafluoropropane In the followings, all the reactions were conducted under a nitrogen atmosphere, and the reagents and solvents used had been dehydrated.

An autoclave was charged with 15 g (28.9 mmol) of 2,2-bis[4-(4-aminophenoxy)phenyl]hexafluoropropane, 7.62 ml (72.3 mmol) of o-fluoronitrobenzene, 6.5 g (161 mmol) of magnesium oxide and 75 ml of water, and the temperature of the autoclave was elevated to 250° C. with stirring. The reaction was continued for 12 hours at the same temperature. After the completion of the reaction, the system was cooled to the room temperature, and 800 ml of ethyl acetate and 300 ml of water were added thereto. Stirring was continued until the generated substance was dissolved in ethyl acetate. The obtained solution was filtered with cerite and extraction with ethyl acetate was conducted twice. Washing was carried out with 1N-hydrochloric acid, saturated aqueous solution of sodium hydrogen carbonate and then with saturated saline, followed by drying with absolute magnesium persulfate and the solvent was removed under reduced pressure. The resulting crude product was refined by using silica gel chromatography (hexane: ethyl acetate=5:1) and re-crystallized by using an ethanol-water mixed solution to obtain 15 g of 2,2-bis[N-(2-nitrophenyl)-{4-(4- aminophenoxy)phenyl}]hexafluoropropane in an orange crystal (yeild: 68%).

The obtained product is a new compound which has the following properties:
Melting point: 117.5 to 118.1° C.
$^1$H-NMR(in CDCl$_3$): δ (ppm)=6.74 to 8.28 (m, 24H), 9.41 to 9.50 (broad, 2H).
$^{19}$F-NMR(in CDCl$_3$): δ (ppm)=−64.4 (s, CF$_3$).
IR(KBr):cm$^{-1}$=3346, 1612, 1577, 1501, 1349, 1248.
MS m/z=760(M+).
HRMS:C$_{39}$H$_{26}$F$_6$N$_4$O$_6$(M+).
Calculated value=760.175.
Measured value=760.176.

Synthesis of 2,2-bis[N-(2-aminophenyl)-{4-(4-aminophenoxy)phenyl}]hexafluoropropane 15 g (19.7 mmol) of 2,2-bis[N-(2-nitrophenyl)-{4-(4-aminophenoxy)phenyl}]hexafluoropropane synthesized above were dissolved in 200 ml of ethyl acetate. Thereto was added 800 mg of 10% palladium carbon as a catalyst, and replacement with hydrogen was then carried out. After that, reaction was conducted at room temperature under a hydrogen pressure of 1.01 MPa (10 atm) for 18 hours with stirring vigorously. The obtained reaction solution was filtered with cerite to remove the catalyst, and ethyl acetate was removed under reduced pressure. The obtained crude product was refined by using silica gel chromatography (hexane: ethyl acetate=2:1), and recrystallized by using a chloroform-hexane mixed solution, and ethanol-water mixed solution to obtain 12.4 g of 2,2-bis[N-(2-aminophenyl)-{4-(4-aminophenoxy)phenyl}]hexafluoropropane (hereinafter EPNPN) in white solid (yeild: 90%).

The synthesized product is a new compound which has the following properties:
Melting point: 62.4 to 64.1° C.
Purity: (LC area %: silica gel column, developing solvent: acetonitrile: 0.05% aqueous solution of phosphoric acid= 80:20):99%.
$^1$H-NMR(in CDCl$_3$): δ (ppm)=6.72 to 7.32 (m, 24H), 3.00 to 3.85 (broad, 4H), 4.85 to 5.25 ppm (broad, 2H).
$^{19}$F-NMR(in CDCl$_3$): δ (ppm)=−64.8 (s, CF$_3$).
IR(KBr):cm$^{-1}$=3375, 3031, 1612, 1513, 1243.
MS m/z=700(M+).
HRMS: C$_{39}$H$_{30}$F$_6$N$_4$O$_2$(M+).
Calculated value=700.227.
Measured value=700.226.

SYNTHESIS EXAMPLE 3

Synthesis of (2,2-bis[N-(2-nitrophenyl)-(3-aminophenyl)] hexafluoropropane

In the followings, all the reactions were conducted under a nitrogen atmosphere, and the reagents and solvents used had been dehydrated.

An autoclave was charged with 20 g (59.8 mmol) of 2,2-bis (3-aminophenyl)hexafluoropropane, 15.8 ml (150.2 mmol) of o-fluoronitrobenzene, 13.5 g (335 mmol) of magnesium oxide and 100 ml of water, and the temperature of the autoclave was elevated to 250° C. with stirring. The reaction was continued for 12 hours at the same temperature. After the completion of the reaction, the system was cooled to the room temperature, and 800 ml of ethyl acetate and 300 ml of water were added thereto. Stirring was continued until the generated substance was dissolved in ethyl acetate. The obtained solution was filtered with cerite and extraction with ethyl acetate was conducted twice. Washing was carried out with 1N-hydrochloric acid, saturated aqueous solution of sodium hydrogen carbonate and then with saturated saline, followed by drying with absolute magnesium persulfate and the solvent was removed under reduced pressure. The resulting crude product was recrystallized using ethanol to obtain 22.4 g of 2,2-bis[N-(2-nitrophenyl)-(4-aminophenyl)] hexafluoropropane in an orange crystal (yeild: 65%).

The obtained product is a new compound which has the following properties:
Melting poing: 151.5 to 157.1° C.
$^1$H-NMR(in CDCl$_3$): δ (ppm)=6.75 to 8.25 (m, 16H), 9.41 to 9.50(broad, 2H).
$^{19}$F-NMR(in CDCl$_3$): δ (ppm)=−64.4(s, CF$_3$).
IR(KBr):cm$^{-1}$=3348, 1605, 1577, 1508, 1346, 1262.
MS m/z=576(M+).
HRMS: C$_{27}$H$_{18}$F$_6$N$_4$O$_4$(M+).
Calculated value=576.123.
Measured value=576.124.

Synthesis of (2,2-bis[N-(2-aminophenyl)-(3-aminophenyl] hexafluoropropane 20 g (34.7 mmol) of 2,2-bis[N-(2-nitrophenyl)-(3-aminophenyl)]hexafluoropropane synthesized above were dissolved in 200 ml of ethyl acetate. Thereto was added 1 g of 10% palladium carbon as a catalyst, and replacement with hydrogen was carried out. After that, reaction was conducted at room temperature under a hydrogen pressure of 1.01 MPa (10 atm) for 18 hours with stirring vigorously. The obtained reaction solution was filtered with cerite to remove the catalyst, and ethyl acetate was removed under reduced pressure. The residue was recrystallized by using a chloroform-hexane mixed solution, and ethanol-water mixed solution to obtain 17 g of 2,2-bis[N-(2-aminophenyl)-(3-aminophenyl)]hexafluoropropane (hereinafter mNPN-AF) in white solid(yeild: 95%).

The synthesized product is a new compound which has the following properties:
Melting point: 175.7 to 176.4° C.
Purity: (LC area %: silica gel column, developing solvent: acetonitrile: 0.05% aqueous solution of phosphoric acid): 98%.
$^1$H-NMR(in CDCl$_3$): δ (ppm)=6.73 to 7.27 (m, 16H), 3.65 to 3.90(broad, 4H), 5.25 to 5.35 ppm (broad, 2H).
$^{19}$F-NMR(in CDCl$_3$): δ (ppm)=−64.8 (s, CF$_3$).
IR(KBr):cm$^{-1}$=3050, 2942, 1510, 1392, 1238.
MS m/z=516(M+).
HRMS: C$_{27}$H$_{22}$F$_6$N$_4$(M+).
Calculated value=516.174.
Measured value=516.174.

EXAMPLE 1

A crosslinkable fluorine rubber composition was produced by mixing the fluorine-containing elastomer having a carboxyl group at the terminal and a nitrile group obtained in Preparation Example 1, the new crosslinking agent (pNPN-AF) obtained in Synthesis Example 1, and carbon black (Thermax N-990, available from Cancarb) which is a filler according to a weight ratio of 100/2.83/20 and then kneading on an open roller.

This fluorine-rubber composition was crosslinked by pressing for 10 minutes at 200° C. and then subjected to a two step crosslinking in the oven under the conditions indicated in Table 4, to prepare test samples of crosslinked product of a 2 mm thickness and O-rings (AS 568A-214). The results measuring the crosslinkability, properties under normal conditions and permanent compression strain of the crosslinked product are shown in Table 4.

(Crosslinkability)

For each crosslinkable composition, using a JSR model curastometer II, the vulcanization curve at the temperature indicated in Table 4 was found, and from this the lowest viscosity (v min), the highest viscosity (v max), the induction period ($T_{10}$) and the optimal vulcanization time ($T_{90}$) were found.

(Properties Under Normal Conditions)

According to JIS K6301, the 100% modulus, tensile strength, tensile elongation and hardness (JIS A hardness) of the crosslinked product of a 2 mm thickness was measured.

(Permanent Compression Strain)

According to JIS K6301, the permanent compression strain of the O-ring (AS-568A-2 14) after 300° C.×70 hours and 300° C.×168 hours was measured.

EXAMPLE 2

An O-ring was prepared in the same manner as in Example 1, except that mNPN-AF obtained in Synthesis Example 3 was used as a crosslinking agent, kneading was conducted with the compounding ratio of fluorine-containing elastomer containing nitrile/mNPN-AF/carbon black as 100/2.83/20 (weight ratio) and crosslinking by pressing was conducted at 200° C. for 15 minutes. Each of the properties was measured in the same way as in Example 1 and the results are shown in Table 4.

EXAMPLE 3

An O-ring was prepared in the same manner as in Example 1 except that EPNPN obtained in Synthesis Example 2 was used as a crosslinking agent, kneading was conducted with the compounding ratio of fluorine-containing elastomer containing nitrile/EPNPN/carbon black as 100/3.84/20 (weight ratio) and crosslinking by pressing was conducted at 200° C. for 60 minutes. Each of the properties was measured in the same way as in Example 1 and the results are shown in Table 4.

TABLE 4

|  | Example | | |
| --- | --- | --- | --- |
|  | 1 | 2 | 3 |
| Component of Composition | | | |
| CN-containing elastomer | 100 | 100 | 100 |
| pNPN-AF | 2.83 | | |
| mNPN-AF | | 2.83 | |
| EPNPN | | | 3.84 |
| Carbon black | 20 | 20 | 20 |
| Crosslinking property (200° C.) | | | |
| Lowest viscosity (N) | 1.27 | 1.67 | 1.86 |
| Highest viscosity (N) | 20.5 | 24.6 | 13.6 |
| Induction period (minute) | 3.5 | 2.1 | 8.3 |
| Optimal vulcanization time (minute) | 7.9 | 5.0 | 55 |
| Properties under normal condition | | | |
| 100% modulus (MPa) | 6.83 | 7.37 | 7.37 |
| Tensile strength (MPa) | 16.0 | 17.7 | 18.9 |
| Elongation (%) | 161 | 164 | 178 |
| Hardness (JIS A) | 74 | 73 | 74 |
| Permanent compression strain | | | |
| 300° C. × 70 hours (%) | 37 | 34 | 47 |
| 300° C. × 168 hours (%) | 59 | 47 | 64 |

As shown in Table 4, in the case that the crosslinking agent of the present invention is used, a crosslinking product superior in heat resistance and permanent compression strain can be obtained.

INDUSTRIAL APPLICABILITY

The present invention can provide a new crosslinkable elastomer composition and a crosslinking agent, which offers a crosslinked product with superior chemical resistance and mechanical strength and improved heat resistance.

What is claimed is:

1. A crosslinkable elastomer composition comprising,
   (A) a compound having at least two crosslinkable groups represented by the formula (I):

and
   (B) an elastomer which contains a crosslinking site capable of reacting with the crosslinkable group (I).

2. The composition of claim 1, wherein said compound (A) is a compound represented by the formula (II):

in which $R^1$ represents a substituted or non-substituted alkylene group, a substituted or non-substituted arylene group, or a group represented by the formula (III):

in which $R^2$ represents —$SO_2$—, —O—, —CO—, a substituted or nonsubstituted alkylene group, or a single bonding.

3. The composition of claim 2, wherein $R^2$ in the formula (III) is a non-substituted alkylene group having 1 to 6 carbon atoms or a fluoroalkylene group having 1 to 10 carbon atoms.

4. The composition of claim 3, wherein $R^2$ in the formula (III) is

5. The composition of claim 1, wherein said elastomer (B) contains at least a functional group selected from the group consisting of a nitrile group, a carboxyl group and an alkoxycarbonyl group as the crosslinking site.

6. The composition of claim 1, wherein said elastomer (B) is a fluorine-containing elastomer.

7. The composition of claim 6, wherein said fluorine-containing elastomer (B) is a perfluoro elastomer.

8. A crosslinking agent comprising,

(A) a compound having at least two crosslinkable groups represented by the formula (I):

9. The crosslinking agent of claim 8, wherein said compound (A) is a compound represented by the formula (II):

in which $R^1$ represents a substituted or non-substituted alkylene group, a substituted or non-substituted arylene group or a group represented by the formula (III):

in which $R^2$ represents —$SO_2$—, —O—, —CO—, a substituted or nonsubstituted alkylene group, or a single bonding.

10. The crosslinking agent of claim 9, wherein $R^2$ in the formula (III) is a non-substituted alkylene group having 1 to 6 carbon atoms or a fluoroalkylene group having 1 to 10 carbon atom.

11. The crosslinking agent of claim 10, wherein $R^2$ the formula (III) is

12. A compound represented by the formula (IV):

in which $R^3$ is

13. A molded article of crosslinked rubber, obtained by crosslinking the crosslinkable elastomer composition of claim 1.

14. The composition of claim 2, wherein said elastomer (B) contains at least a functional group selected from the group consisting of a nitrile group, a carboxyl group and an alkoxycarbonyl group as the crosslinking site.

15. The composition of claim 2, wherein said elastomer (B) is a fluorine-containing elastomer.

16. A molded article of crosslinked rubber, obtained by crosslinking the crosslinkable elastomer composition of claim 2.

* * * * *

UNITED STATES PATENT AND TRADEMARK OFFICE
CERTIFICATE OF CORRECTION

PATENT NO. : 6,855,774 B2
DATED : February 15, 2005
INVENTOR(S) : Kazuyoshi Kawasaki et al.

It is certified that error appears in the above-identified patent and that said Letters Patent is hereby corrected as shown below:

<u>Title page,</u>
Item [30], Foreign Application Priority Data, delete "Feb. 11, 2003" and insert -- June 27, 2000 --

Signed and Sealed this

Seventeenth Day of May, 2005

JON W. DUDAS
*Director of the United States Patent and Trademark Office*